(12) United States Patent
Carvin et al.

(10) Patent No.: US 7,270,752 B2
(45) Date of Patent: Sep. 18, 2007

(54) PROCESS FOR PURIFYING LACTAMS

(75) Inventors: Philippe Carvin, Lyons (FR);
Jean-Claude Masson, Lyons (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 10/169,111

(22) PCT Filed: Dec. 27, 2000

(86) PCT No.: PCT/FR00/03694

§ 371 (c)(1),
(2), (4) Date: Jan. 27, 2003

(87) PCT Pub. No.: WO01/49665

PCT Pub. Date: Jul. 12, 2001

(65) Prior Publication Data

US 2003/0155299 A1    Aug. 21, 2003

(30) Foreign Application Priority Data

Dec. 30, 1999   (FR) ................................. 99 16713

(51) Int. Cl.
*B01D 9/02* (2006.01)
*B01D 9/00* (2006.01)
*C07D 223/10* (2006.01)

(52) U.S. Cl. ................... 210/634; 23/299; 23/301; 210/749; 210/669; 210/806; 540/485

(58) Field of Classification Search ................ 210/634, 210/663, 669, 774, 749, 806; 540/538, 540, 540/485; 203/48; 117/11, 68; 23/295, 301, 23/299

See application file for complete search history.

(56) References Cited

U.S. PATENT DOCUMENTS

| | | | | | |
|---|---|---|---|---|---|
| 3,080,345 | A | * | 3/1963 | Brooks et al | 428/397 |
| 3,400,087 | A | * | 9/1968 | Robb et al. | 524/385 |
| 5,440,032 | A | * | 8/1995 | Hirosawa et al. | 540/540 |
| 5,496,941 | A | * | 3/1996 | Ritz et al. | 540/540 |
| 5,502,184 | A | * | 3/1996 | Kajikuri et al. | 540/536 |
| 6,252,068 | B1 | * | 6/2001 | Fukao et al. | 540/540 |

FOREIGN PATENT DOCUMENTS

| | | |
|---|---|---|
| CH | 564 528 | 7/1975 |
| DE | 1 022 591 | 1/1958 |
| DE | 1 620 756 | 7/1970 |
| EP | 0 010 271 B1 | 4/1980 |
| EP | 0 337 323 B1 | 7/1995 |
| EP | 0 826 665 A1 | 3/1998 |
| EP | 0 943 608 A1 | 9/1999 |
| JP | 7-179419 A | 7/1995 |

OTHER PUBLICATIONS

Search Report issued in International Application No. EP 0 943 608 A1.

* cited by examiner

*Primary Examiner*—Joseph Drodge
(74) *Attorney, Agent, or Firm*—Buchanan, Ingersoll & Rooney, PC

(57) ABSTRACT

A process is described for purifying lactams, in particular the lactams obtained by cyclizing hydrolysis of an aminoalkylnitrile, and more particularly to the purification by crystallization of $\epsilon$-caprolactam obtained by cyclizing hydrolysis of aminocapronitrile. This crystallization is carried out on the cyclization reaction medium after hydrogenation, removal of volatile compounds, and treatment with an ion-exchange resin.

11 Claims, No Drawings

PROCESS FOR PURIFYING LACTAMS

This application is a 371 of PCT/FR00/03694, filed Dec. 27, 2000, published in French as WO 01/49665.

The invention relates to a process for purifying lactams, in particular the lactams obtained by cyclizing hydrolysis of an aminoalkylnitrile.

The invention relates more particularly to the purification of ε-caprolactam obtained by cyclizing hydrolysis of aminocapronitrile.

Lactams and in particular ε-caprolactam are important chemical compounds used as starting materials in the manufacture of many products. One of the most important applications is the manufacture of polymers such as polyamides.

Among the processes for synthesizing lactams and in particular ε-caprolactam which have been proposed is a process consisting in manufacturing an aminoalkylnitrile such as aminocapronitrile and then in carrying out a cyclizing hydrolysis of this aminonitrile. This process, which may be carried out in liquid or gaseous medium with or without solvent, is disclosed, for example, in patents EP 0 729 454, EP 0 729 453, EP 0 793 650, EP 0 793 651, EP 0 794 943, EP 0 815 077, EP 0 815 078, EP 0 748 797, EP 0 6559 741 and WO 96/22974.

An important step in the manufacture of lactams, in particular ε-caprolactam, when these need to be used as monomers in the manufacture of polymers such as polyamides, is the purification of the products. Specifically, for these applications, the lactam must satisfy highly stringent and demanding purity criteria. These criteria are defined by various indices or concentrations corresponding to several types or categories of impurity. These main criteria are:

permanganate number ($I_{KMnO_4}$)
content of volatile bases ($I_{VB}$)
UV index ($I_{UV}$)

Various purification processes have already been proposed. Thus, U.S. Pat. No. 5,496,941 discloses a process for purifying caprolactam extracted from the reaction medium of a cyclizing hydrolysis by distillation comprising a hydrogenation step followed by a treatment in acidic medium (treatment on ion-exchange resin or distillation in sulphuric acid medium) and a distillation in basic medium.

European patent application No. 94/3608 discloses a process for purifying crude ε-caprolactam obtained by cyclization of an alkyl 6-aminocaproate, which consists in carrying out a crystallization of the caprolactam. According to the said document, certain components such as N-methylcaprolactam, methylvalerolactam and valeramide are removed by crystallization. The process disclosed indicates that the caprolactam thus crystallized satisfies the required purity criteria regarding the content of volatile bases and the UV index for absorption at a wavelength of 290 nm.

However, the said document does not specify whether or not the third purity criterion, the permanganate number, is achieved.

In the case of a caprolactam obtained from the cyclizing hydrolysis of an aminocapronitrile obtained by semihydrogenation of adiponitrile, the purity criteria of the caprolactam are achieved by carrying out purification processes described above comprising several successive treatments, in particular an acidic treatment and a final distillation in basic medium.

In such processes, the production of a caprolactam of the desired purity requires the implementation of a distillation operation with a large heavy fraction (fraction of products with a high boiling point) comprising a large amount of lactam in the form of lactam or oligomers. This loss of lactam is detrimental to the process.

One of the aims of the present invention is especially to overcome this drawback by proposing a process for purifying lactams making it possible to obtain a product that satisfies the desired purity criteria, thus limiting the lactam treatment steps and more particularly those which may generate the formation of oligomers.

To this end, the invention proposes a process for purifying a lactam obtained from the cyclization of an aminoalkylnitrile obtained by semihydrogenation of an alkyldinitrile, which consists, after removing the volatile compounds from the cyclization medium, in extracting the lactam formed by crystallization.

According to another preferred characteristic of the invention, the crystalline lactam can be subjected to one or more other crystallization steps to obtain the desired purity. Other purification treatments may be carried out on the crystalline lactam without departing from the scope of the present invention.

According to another embodiment, the cyclization medium may be subjected to a hydrogenation before the step to remove the volatile compounds According to yet another embodiment, the crystallization of the caprolactam is carried out on the cyclization medium which may or may not have undergone a hydrogenation, after treating this medium in acid medium, for example by passing it through an ion-exchange resin or a distillation in acidic medium.

According to another embodiment, a hydrogenation of the cyclization medium may be carried out after removing tie volatile compounds.

For simplicity, the expression "cyclization medium" for carrying out the crystallization means either the reaction medium obtained from the cyclization step on which the various treatments described above are carried out, or the medium formed by the caprolactam extracted after the cyclization reaction, for example by distillation or entrainment, in other words after removal or separation of the volatile compounds and the high-boiling compounds. The classification into volatile compounds and high-boiling compounds is made relative to the boiling point of the lactam to be recovered.

According to the invention, the extraction and recovery of the lactam by a crystallization make it possible to obtain a product which satisfies the desired purity criteria, without the need for treatment at temperatures which may generate the formation of oligomers, for example.

Thus, the degradation or polymerization of the lactam, which arises when it is heated to high temperatures, especially in order to distil it, is avoided.

The process of the invention applies more particularly to the purification of ε-caprolactam obtained by cyclizing hydrolysis of aminocapronitrile.

This aminocapronitrile is synthesized by semihydrogenation of adiponitrile. These various semihydrogenation processes are disclosed, for example, in patents EP 0 737 100, EP 0 737 181 and WO 96/18603.

According to the invention, the solvents that are suitable for the crystallization may be a lactam, water, saturated hydrocarbons such as hexane or cyclohexane, alcohols, aromatic hydrocarbons, organohalogen compounds such as $CCl_4$ or $CHCl_3$, ketones or the like.

Solvents that well preferably be used include water and/or a lactam and more preferably a lactam which is identical to the one which needs to be purified, or, more preferably, a saturated aqueous lactam solution.

The crystallization may be carried out in one step or in several steps. The mother liquor obtained in one step is advantageously recycled into one of the preceding steps. More generally, the crystallization may be carried out according to the conventional industrial crystallization techniques.

According to another characteristic of the process of the invention, the compound obtained after crystallization is filtered off, spin-filtered or isolated by any other common solid/liquid separation technique. The solid recovered may be advantageously washed with a solvent, preferably with a saturated lactam solution.

Advantageously, the medium containing the lactam to be crystallized is concentrated by any means which is suitable to obtain a weight concentration of lactam of greater than 80% by weight, preferably greater than 90%.

Thus, examples of techniques for saturating or concentrating the solution which may be mentioned include techniques of cooling and evaporation advantageously under reduced pressure to work at lower temperature.

In addition, the crystallization can be performed with seeding of the solution in order to promote nucleation of the lactam.

The pure lactam recovered after solid/liquid separation, for example filtration, and optional washing, is dried or the solvent, for example water, is distilled off according to usual techniques (when the solvent is water, the caprolactam is dehydrated).

The process of the invention thus makes it possible to produce a lactam, more particularly an ε-caprolactam, which has the desired purity criteria for use as monomer in the manufacture of polyamides such as PA6. The polyamides thus obtained are suitable in particular for the manufacture of textile yarns or fibres with working properties that are equivalent to those of the current polyamides.

Other advantages and details of the invention will be illustrated by the implementation examples below, given purely as a guide.

EXAMPLE 1

An ε-caprolactam is manufactured according to the process disclosed in the patents cited above.

Thus, this ε-caprolactam is obtained according to Example 1 of patent EP 0 748 797 by semihydrogenation of adiponitrile followed by cyclizing hydrolysis of aminocapronitrile according to the conditions described in the said example.

The medium obtained is subjected to a hydrogenation according to the process disclosed in the as yet unpublished french patent application filed under No. 98/14735 on Nov. 19, 1998.

The ammonia present in the hydrogenated cyclizing hydrolysis reaction medium is then removed by evaporation or entrainment.

The cyclization medium thus obtained is then treated by passing it through an ion-exchange resin according to the conditions disclosed in the patents or patent applications WO 98/05636 or WO 96/20923.

The medium obtained after treatment with resin contains 65% by weight of ε-caprolactam and numerous other products which were not all identified.

The medium thus recovered is analysed to determine the purity criteria defined above. The results of these analyses are indicated in the table below.

In accordance with the process of the invention, the caprolactam is recovered by crystallization from this solution after concentration under reduced pressure at a caprolactam content in the region of 90% by weight.

The solution is concentrated at a temperature of 40° C. and is then cooled to a temperature in the region of 20° C. at a cooling rate of about 10° C. per hour.

The crystals formed are recovered by filtration on a sinter funnel. The mother liquors recovered are stored for possible recycling.

The sold cake of caprolactam crystals is washed with a saturated aqueous caprolactam solution. The degree of washing with wet base is advantageously between 1 and 5.

The crystalline caprolactam is analysed. The purity characteristics are collated in Table I below.

| Test | Medium | $I_{UV}$ | $I_{KMO4}$ | $I_{VB}$ (meq/kg) |
|---|---|---|---|---|
| | Medium before crystallization | 0.45 | 32.06 | 2.69 |
| | Wet cake after washing | 0.02 | 2.03 | 0.04 |

EXAMPLE 2

A caprolactam is manufactured according to the process described in Example 1 and with reference to the process disclosed in patent application EP 0 748 797.

However, in this example, the medium obtained from the cyclizing hydrolysis is only treated to remove the volatile compounds, more particularly ammonia.

The crystallization of the caprolactam formed is carried out directly using this solution after concentration by evaporation of water.

The crystallization is carried out in two successive steps. The cake recovered in the first step is taken up to give a new saturated aqueous solution and is then recrystallized. The purity characteristics of the cake recrystallized after washing are given in Table II below.

| Test | Medium | $I_{UV}$ | $I_{KMO4}$ | $I_{VB}$ (meq/kg) |
|---|---|---|---|---|
| 2 | Medium before crystallization | 17.7 | 400 | 130 |
| | Wet cake recrystallized after washing | 0.03 | 2.0 | 0.20 |

The invention claimed is:

1. A process for purifying lactams from a cyclization medium obtained by cyclization of aminoalkylnitriles, without a treatment at high temperatures which generates degradation or polymerization of said lactams which comprises:
    hydrogenating a cyclization medium obtained from the cyclization reaction;
    removing volatile compounds from the cyclization medium;
    treating the cyclization medium with an ion-exchange resin; and
    recovering the lactam by crystallization from the cyclization medium, wherein crystallization is effected by seeding to promote nucleation of the lactam;
    wherein the steps of hydrogenating a cyclization medium obtained from the cyclization reaction, removing volatile compounds from the cyclization medium, and treating the cyclization medium with an ion-exchange resin, are conducted prior to crystallization of the cyclization medium.

2. Process according to claim 1, wherein the crystallization is carried out in several steps.

3. Process according to claim 1, wherein the hydrogenation occurs before removing the volatile compounds.

4. Process according to claim 1, wherein the hydrogenation occurs after separation of the volatile compounds.

5. Process according to claim 1, wherein the lactam is ε-caprolactam.

6. Process according to claim 5, wherein the ε-caprolactam is produced by cyclizing hydrolysis of aminocapronitrile.

7. Process according to claim 6, wherein the aminocapronitrile is synthesized by semihydrogenation of adiponitrile.

8. Process according to claim 1, wherein a solvent is used for crystallization and is selected from the group consisting of a lactam, an aqueous lactam solution, water, saturated hydrocarbons, alcohols, aromatic hydrocarbons, organohalogen compounds and ketones.

9. Process according to claim 8, wherein the solvent is a saturated aqueous lactam solution.

10. Process according to claim 1, wherein the weight concentration of lactam in the cyclization medium to be crystallized is greater than 80% by weight.

11. The process according to claim 1, wherein the lactam obtained after crystallization is filtered off, spin-filtered or isolated by solid/liquid separation.

* * * * *